(12) United States Patent
Varga

(10) Patent No.: US 10,159,812 B2
(45) Date of Patent: Dec. 25, 2018

(54) FLOW SPLITTING NCPAP DEVICE

(75) Inventor: Christopher M. Varga, Laguna Hills, CA (US)

(73) Assignee: CareFusion 207, Inc., San Diego, CA (US)

(*) Notice: Subject to any disclaimer, the term of this patent is extended or adjusted under 35 U.S.C. 154(b) by 125 days.

(21) Appl. No.: 13/074,990

(22) Filed: Mar. 29, 2011

(65) Prior Publication Data

US 2012/0247480 A1   Oct. 4, 2012

(51) Int. Cl.
| A62B 7/00 | (2006.01) |
| A61M 16/00 | (2006.01) |
| A61M 16/06 | (2006.01) |
| A61M 16/12 | (2006.01) |
| A61M 16/08 | (2006.01) |

(52) U.S. Cl.
CPC ........ *A61M 16/0096* (2013.01); *A61M 16/06* (2013.01); *A61M 16/0666* (2013.01); *A61M 16/0858* (2014.02); *A61M 16/125* (2014.02); *A61M 16/0816* (2013.01); *A61M 2016/0027* (2013.01); *A61M 2206/10* (2013.01); *A61M 2210/0618* (2013.01); *F04C 2270/041* (2013.01)

(58) Field of Classification Search
CPC ...... A61M 2210/0618; A61M 16/0683; A61M 25/02; A61M 16/06–16/0694; A61M 2016/0616; A61M 16/0666; A62B 7/00; A62B 7/14; A62B 18/00; A62B 18/02; A62B 18/04; A62B 18/06; A62B 18/08–18/088
USPC ............ 128/200.24, 200.26, 203.22, 206.11, 128/207.13, 207.18; 137/823
See application file for complete search history.

(56) References Cited

U.S. PATENT DOCUMENTS

| 5,099,836 A * | 3/1992 | Rowland et al. ........ 128/204.23 |
| 5,193,532 A | 3/1993 | Moa et al. |
| 5,687,715 A * | 11/1997 | Landis .............. A61M 16/0633 128/204.18 |
| 5,975,077 A | 11/1999 | Hofstetter et al. |
| 7,905,232 B2 | 3/2011 | Olsen et al. |
| 2003/0000527 A1 | 1/2003 | Stenzler et al. |
| 2003/0200970 A1* | 10/2003 | Stenzler et al. ......... 128/207.18 |
| 2004/0065330 A1 | 4/2004 | Landis |
| 2004/0094157 A1* | 5/2004 | Dantanarayana et al. ................... 128/206.21 |
| 2005/0011524 A1* | 1/2005 | Thomlinson et al. ... 128/207.18 |
| 2006/0130840 A1 | 6/2006 | Porat et al. |

(Continued)

FOREIGN PATENT DOCUMENTS

| JP | 2002533174 A | 10/2002 |
| RU | 2411920 C1 | 2/2011 |

OTHER PUBLICATIONS

International Search Report and Written Opinion for PCT/US2012/028962 dated Oct. 12, 2012.

(Continued)

*Primary Examiner* — Gregory Anderson
*Assistant Examiner* — Ned T Heffner
(74) *Attorney, Agent, or Firm* — Morgan, Lewis & Bockius LLP

(57) ABSTRACT

A nCPAP device includes an net configured for receiving a single gas jet flow. The single gas jet flow supplies gas for both nares. The device also includes a flow splitter configured for proportionally splitting said gas jet flow into two channels for the both nares according to one or more of nave anatomy and flow path resistance.

19 Claims, 5 Drawing Sheets

(56) References Cited

U.S. PATENT DOCUMENTS

| | | | |
|---|---|---|---|
| 2006/0174885 A1* | 8/2006 | Aylsworth et al. | 128/206.11 |
| 2007/0125379 A1* | 6/2007 | Pierro et al. | 128/204.23 |
| 2008/0047559 A1* | 2/2008 | Fiori | 128/206.11 |
| 2008/0060657 A1 | 3/2008 | McAuley et al. | |
| 2009/0241948 A1 | 10/2009 | Clancy et al. | |
| 2010/0326441 A1* | 12/2010 | Zucker et al. | 128/204.18 |
| 2012/0080033 A1* | 4/2012 | Varga et al. | 128/204.18 |
| 2012/0080034 A1* | 4/2012 | Mansour et al. | 128/204.25 |

OTHER PUBLICATIONS

Extended European Search Report dated Aug. 25, 2014 for PCT application PCT/US2012/028962.
Japanese Office Action for Application No. 2014-502614, dated Dec. 22, 2015, 4 pages excluding translation.
Russian Office Action for Application No. 2013142749, dated Jan. 25, 2016, 5 pages excluding translation.
Mexican Office Action for Application No. MX/a/2013/010769, dated Apr. 12, 2016, 4 pages excluding machine translation.
Russian Office Action for Application No. 2013142749, dated Apr. 11, 2016, 4 pages excluding translation.
European Office Action for Application No. 12763246.1, dated Feb. 23, 2017, 5 pages.
Mexican Office Action for Application No. MX/a/2013/010769, dated Jan. 11, 2017, 3 pages excluding machine translation.
Japanese Office Action for Application No. 2014-502614, dated Aug. 30, 2016, 3 pages excluding translation.
Mexican Second Office Action for Application No. MX/a/2013/010769, dated Aug. 25, 2016, 2 pages excluding machine translation.
Japanese Patent Application No. 2014-502614, dated Jun. 20, 2017, 4 pages excluding translation.
Japanese Office Action for Application No. 2014-502614, dated Jan. 9, 2018, 3 pages excluding English translation.

* cited by examiner

FLOW SPLITTING NCPAP DEVICE

BACKGROUND

Continuous positive airway pressure (CPAP) support and/or non-invasive ventilation are commonly used to facilitate spontaneous breathing of infants with respiratory distress. Variable flow nasal CPAP devices typically utilize at least two jets (one for each nare) to provide the requisite airway pressure. CPAP devices that utilize at least two jets can be obtrusive and bulky with respect to the small size of infants. Moreover, the construction of such devices is often complex to produce the multiple jet arrangements.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Continuous positive airway pressure (CPAP) therapy is employed to treat patients experiencing respiratory difficulties and/or insufficiencies. In addition, CPAP therapy can beneficially assist patients with under-developed lungs (in particular, infants and especially premature infants or neonates) by preventing lung collapse during exhalation and assisting lung expansion during inhalation.

In general, CPAP therapy entails the continuous transmission of positive pressure into the lungs of a spontaneously breathing patient throughout the respiratory cycle. CPAP can be delivered to the patient using a variety of patient interface devices, for example an endotracheal tube or nasal cannula. With infants, however, it is more desirable to employ a non-invasive patient interface device, in particular one that interfaces directly or indirectly with the nasal airways via the patient's nares. Such systems are commonly referred as nasal continuous positive airway pressure (nCPAP) systems.

Figure 1A:
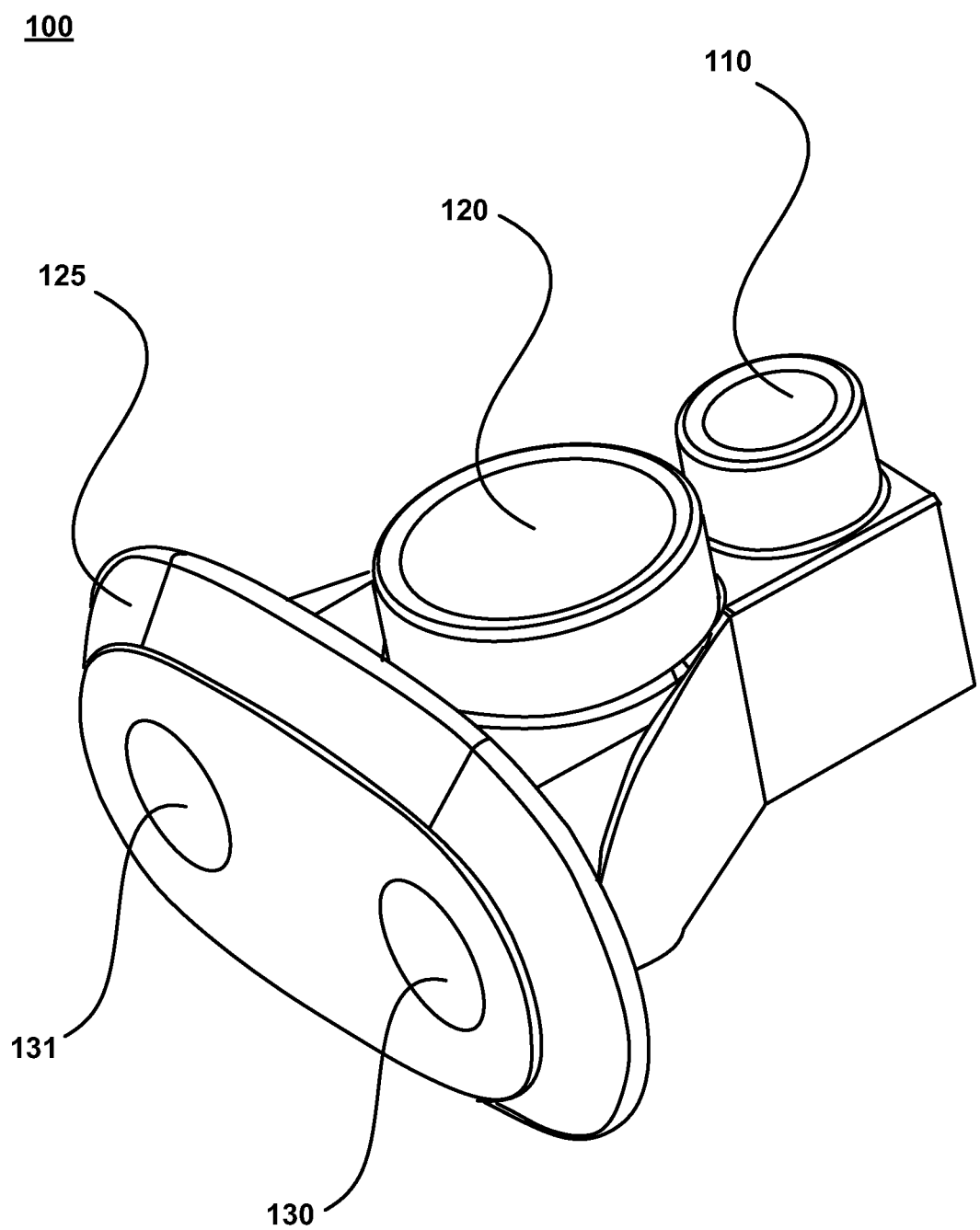
FIGS. 1A-2 illustrate examples of a flow splitting nCPAP device, in accordance with embodiments of the present invention.
Figure 1B:
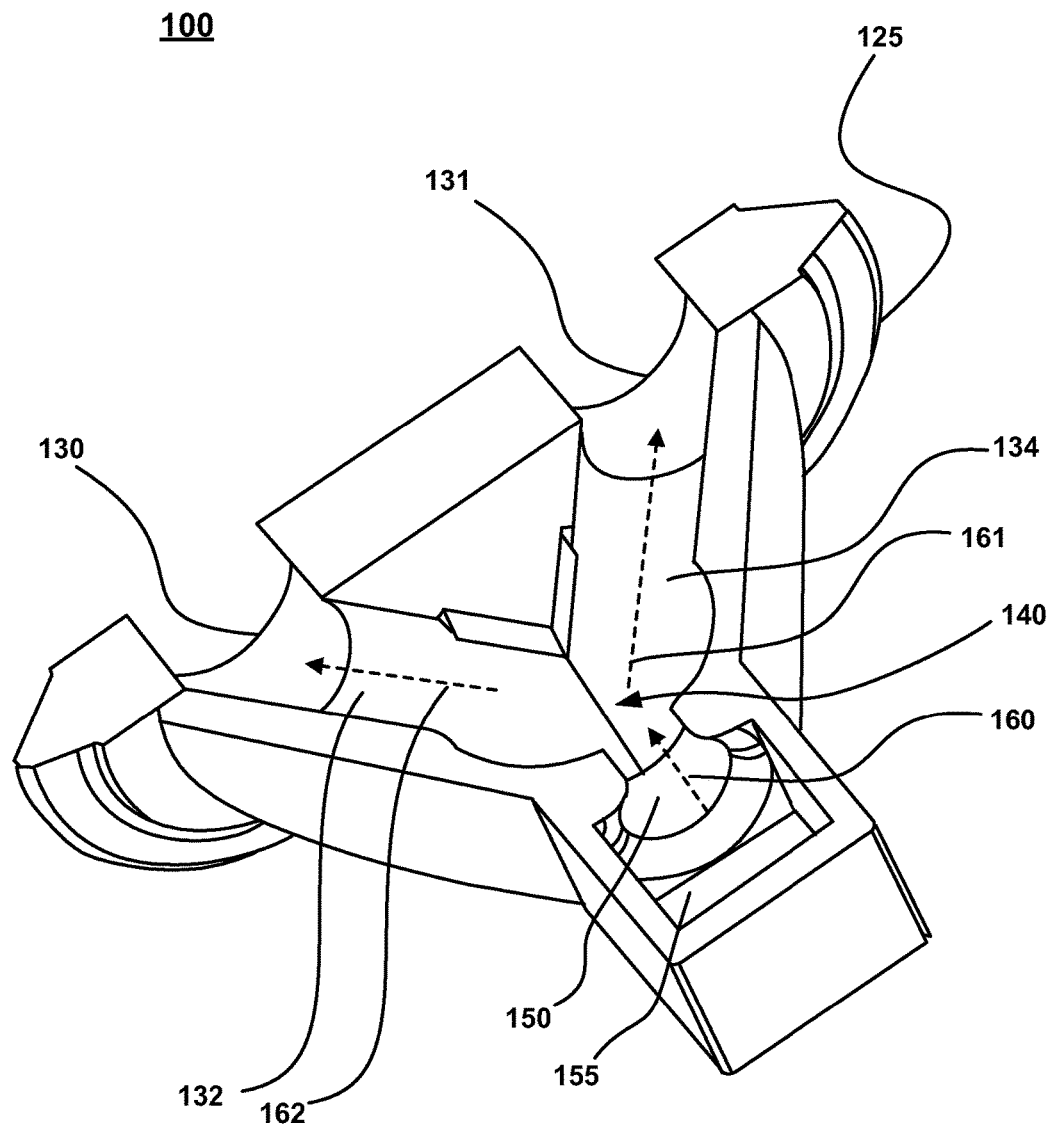
Figure 1C:
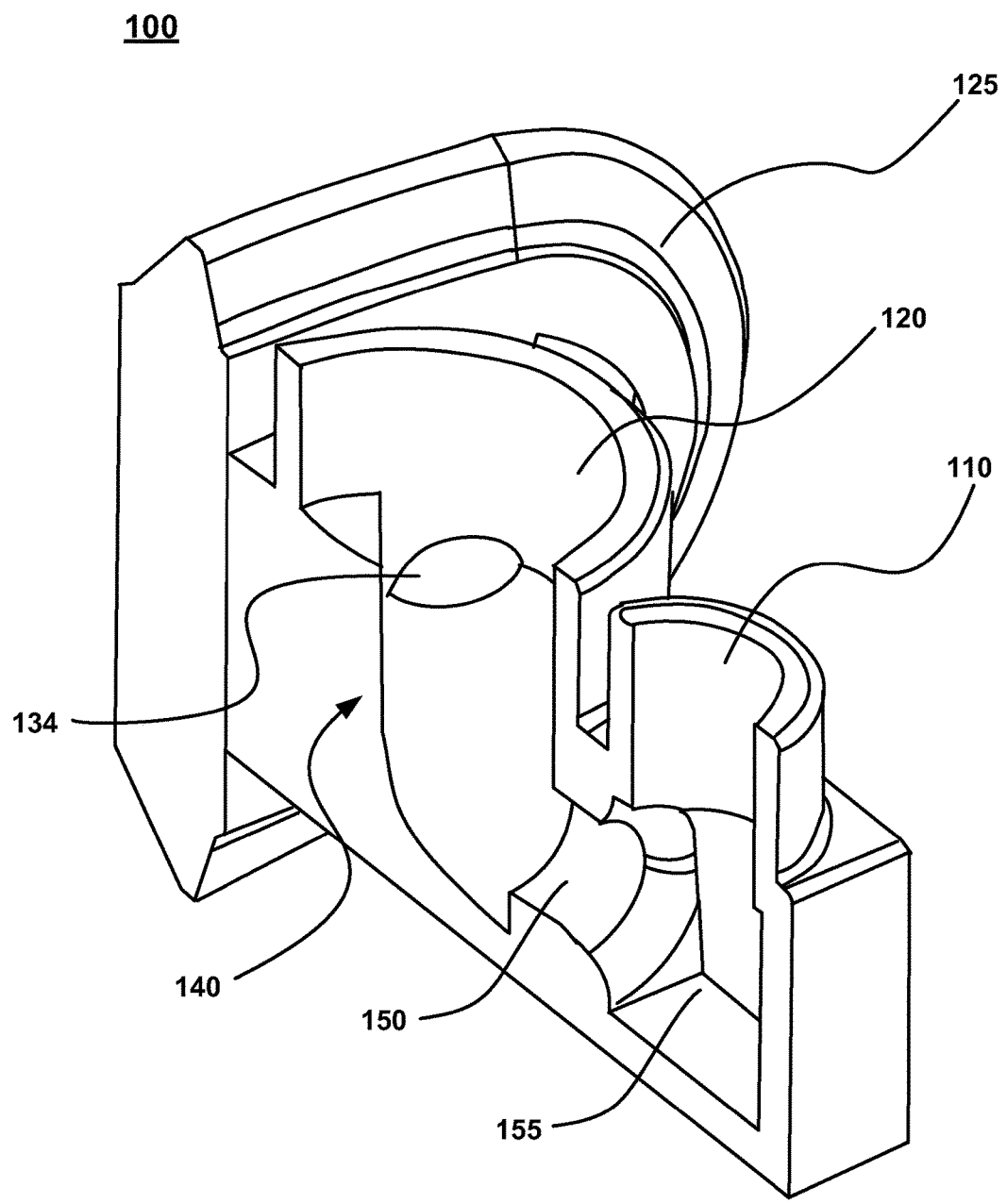

FIGS. 1A-C depict an embodiment of nCPAP device 100 for use in an nCPAP system. In particular, FIGS. 1B-C depict cross-sectional views of nCPAP device 100. In general, device 100 facilitates in providing nCPAP support and/or non-invasive ventilation to spontaneously breathing patients infants) with respiratory distress.

Device 100 includes inlet 110, exhaust port 120, rare ports 130 and 131, channels 132 and 134, nozzle 150, plenum 155 and flow splitter 140.

During use, pressurized gas (e.g., air, oxygen, etc) is provided to inlet 110. The pressurized gas is generated into a single jet flow 160 when it passes through plenum 155 and nozzle 150. The jet is sized such that it utilizes reasonably low supply gas pressures (e.g., those supported by commonly available critical care ventilators) to deliver therapeutic CPAP support levels.

Flow splitter 140 splits jet flow 160 into two channel flows (one channel flow for each nare). For example, jet flow 160 is split into channel flow 161 (that travels through channel 132 and out of port 130) and channel flow 162 (that travels through channel 134 and out of port 131).

Flow splitter 140 includes flow-splitting geometry that faces upstream towards jet flow 160. The flow-splitting geometry serves to deflect and split jet flow 160 as necessary. The flow splitting is self-adjusting and also proportionally splits the jet flow according to relative restrictions of nare anatomy and flow demands of the patient. For example, if the nare corresponding to port 130 requires half the gas supply than the nare corresponding to port 131 (due to anatomy and/or flow demands), then flow splitter 140 proportionally splits jet flow 160 such that channel flow 162 provides half as much gas flow through channel 132 than channel flow 161 flowing through channel 134.

Therefore, device 100 is able to optimally self-adjust overall flow delivery to each nare from a single jet flow (e.g., jet flow 160). Moreover, a nasal CPAP device includes a simplified geometry and operation with reduced complexity and size.

In contrast, prior technologies that utilize at least two jets can be obtrusive and bulky with respect to the small size of infants. Moreover, the construction of such devices is often complex to produce the Multiple jet arrangements.

During an inhalation phase, excess flow (jet flow which is above the level required by the patient's tidal volume) is exhausted out a single exhaust path through exhaust port 120, which is in fluid communication with both branched channels.

Moreover, during inhalation flows where patient demand exceeds the flow rate supplied by jet flow 160, the role of exhaust port 120 is altered to an entrainment port such that the fresh gas jet entrains the necessary excess inhalation flow for patient delivery.

During an exhalation phase, the patient exhalation flow, along with the fresh gas flow, are exhausted together out exhaust port 120. Rapid diversion of the fresh gas jet flow out the exhaust port 120 is promoted by the geometry of device 100. More specifically, by the close proximity of the exhaust port to the jet exit, as well as, by the specific geometry of the flow splitting surface where three flows (the two branched channel exhalation flows and one incoming fresh gas jet flow) meet along a curving edge transition.

In other words, the expiratory airflow causes the jet stream flow to deflect, thus triggering a diversion or flip of the incoming jet flow. As a result, the jet stream and the expiratory airflow readily proceed to the exhaust port, thus reducing the patient's required work-of-breathing.

Figure 2:
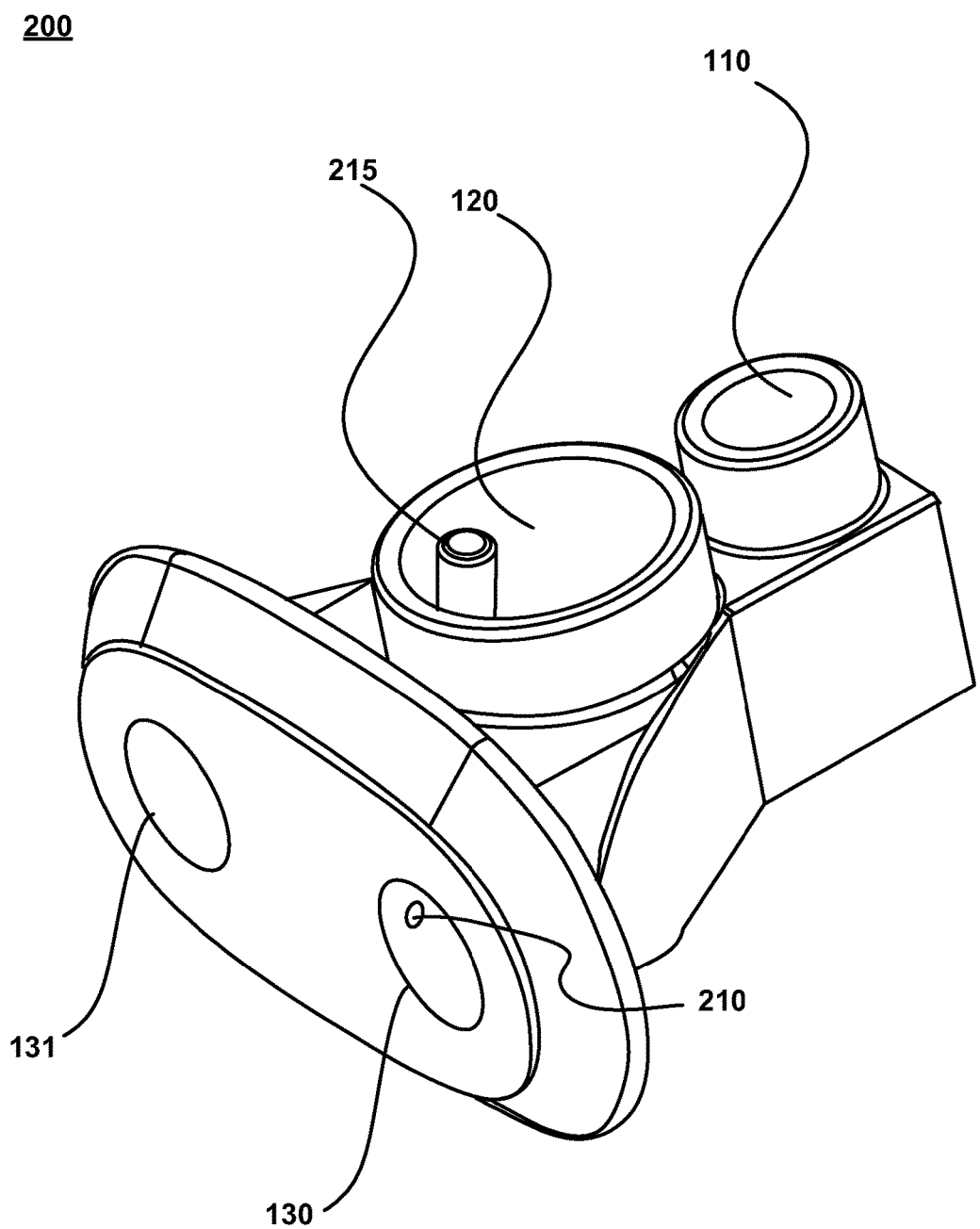

FIG. 2 depicts an embodiment of nCPAP device 200 for use in a nCPAP system. Device 200 is similar to device 100. However, device 200 includes provisions for monitoring the generated CPAP pressure.

In particular, device 200 includes pressure measurement port 210 associated with port 130 and another pressure measurement port (not shown) associated with port 131. The pressure measurement ports are fluidly connected to pressure monitoring port 215, where a pressure line can be connected and routed to a pressure monitor.

It should be appreciated that supplying nCPAP and/or non-invasive ventilation via a single gas jet flow (e.g., jet flow 160) enables simplified construction, reduced size, and/or lower costs of manufacture. Moreover, the jet can be sized to require gas source pressures which are available on common critical-care ventilators.

Figure 3:
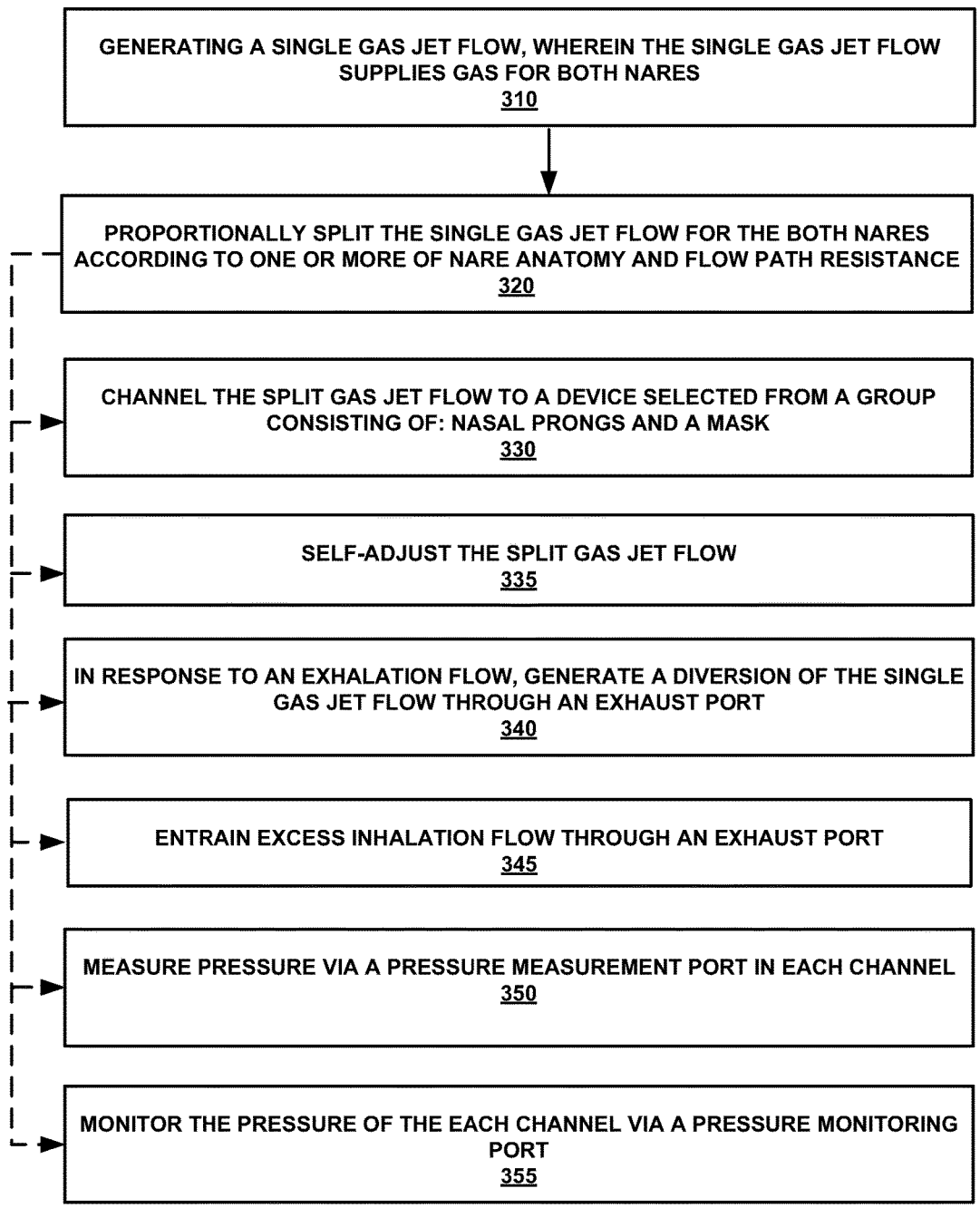
FIG. 3 illustrates an example of a flow chart of a method for splitting a gas jet flow in a nCPAP system, in accordance with an embodiment of the present invention.

FIG. 3 depicts a method 300 for splitting a gas jet flow in a nCPAP system. In various embodiments, method 300 is performed at least by devices 100 or 200, as described above.

At 310 of method 300, a single gas jet flow is generated, wherein the single gas jet flow supplies gas for both nares. For example, only gas jet flow 160 is generated to supply gas flow to the nares of the patient.

At 320, the single gas jet flow is proportionally split for each nare according to one or more of nare anatomy and flow path resistance. For example, gas jet flow 160 is proportionally split into gas channel flow 161 and 162 according to one or more of nare anatomy and flow path resistance.

At 330, the split gas flows are channeled to a device selected from a group consisting of: nasal prongs and a mask. For example, nasal prongs are physically and fluidly associated with ports 130 and 131. In another example, a mask is disposed on interface 125.

At 335, the split gas jet flow is self-adjusted. For example, if a nasal passage way is blocked due to congestion, then gas jet flow 160 is self-adjustingly split into channel flows 161 and 162 with an air flow based on the resistance due to the congestion.

At 340, in response to an exhalation flow, a diversion is generated such that the single gas jet flow is exhausted through an exhaust port.

At 345, excess inhalation flow is entrained through an exhaust port. For example, when patient inhalation flow demand exceeds the flow rate supplied by jet flow 160, the role of exhaust port 120 is altered to an entrainment port such that the fresh gas jet entrains the necessary excess inhalation flow for patient delivery.

At 350, pressure is measured via a pressure measurement port in each channel. For example, pressure is measured via pressure measurement port 210.

At 355, pressure of the each channel via a pressure monitoring port is monitored.

Various embodiments of the present invention are thus described. While the present invention has been described in particular embodiments, it should be appreciated that the present invention should not be construed as limited by such embodiments, but rather construed according to the following claims.

The invention claimed is:

1. A nasal continuous positive airway pressure (nCPAP) device comprising:
   a monolithic block comprising:
      an inlet configured for receiving a single gas jet flow, wherein the single gas jet flow supplies gas for two nares of a patient;
      a substantially triangular-shaped corner comprising a flow splitter configured for proportionally splitting the single gas jet flow into two channels for the nares according to a gas supply capacity of at least one nare of the patient, or flow path resistance of at least one nare of the patient; and
      an exhaust port comprising a fixed aperture larger than an inlet aperture and the two channels for the nares, the exhaust port configured to conduct an expiratory airflow from the two channels for the nares to cause the single gas jet flow to deflect, and the exhaust port is further configured to alter an exhaust role and entrain an excess inhalation when a patient demand exceeds a flow rate supplied by the single gas jet flow wherein an axis perpendicular to the inlet is parallel to an axis perpendicular to the exhaust port.

2. The nasal continuous positive airway pressure (nCPAP) device of claim 1, further comprising:
   an interface configured for interfacing with nasal prongs.

3. The nasal continuous positive airway pressure (nCPAP) device of claim 1, further comprising:
   an interface configured for interfacing with a mask.

4. The nasal continuous positive airway pressure (nCPAP) device of claim 1, wherein the flow splitter is further configured for facilitating a diversion of the single gas jet flow to the exhaust port.

5. The nasal continuous positive airway pressure (nCPAP) device of claim 1, further comprising:
   a pressure measurement port disposed in an exit channel.

6. The nasal continuous positive airway pressure (nCPAP) device of claim 1, further comprising:
   a nozzle for generating the single gas jet flow.

7. The nasal continuous positive airway pressure (nCPAP) device of claim 1, wherein the flow splitter comprises:
   a curving edge transition where at least one branched channel exhalation flow meets and diverts the single gas jet flow into the exhaust port.

8. The nasal continuous positive airway pressure (nCPAP) device of claim 1, wherein the exhaust port is further configured to exhaust the single gas jet flow during exhalation.

9. The nasal continuous positive airway pressure (nCPAP) device of claim 1, wherein the exhaust port is further configured to exhaust a portion of an expiratory airflow.

10. The nasal continuous positive airway pressure (nCPAP) device of claim 1, further comprising a pressure measurement port on each of the two channels for the nares.

11. The nasal continuous positive airway pressure (nCPAP) device of claim 1, further comprising a nozzle configured to provide the single gas jet flow.

12. The nasal continuous positive airway pressure (nCPAP) device of claim 1, wherein the exhaust port is disposed in close proximity to an exit of a nozzle.

13. A method for splitting a gas jet flow in a nasal continuous positive airway pressure (nCPAP) system, the method comprising:
   generating a single gas jet flow, wherein the single gas jet flow supplies gas for two nares of a patient;
   providing the single gas jet flow to a monolithic block, the monolithic block comprising an inlet and an exhaust port, wherein an axis perpendicular to the inlet is parallel to an axis perpendicular to the exhaust port;
   proportionally splitting, in the monolithic block, and by a substantially triangular-shaped corner comprising a flow splitter the single gas jet flow for the nares according to a gas supply capacity of at least one nare of the patient, or flow path resistance of a nare of the patient;
   diverting, with least one branched channel exhalation flow, the single gas jet flow into the exhaust port along a curving edge transition in the flow splitter, wherein the exhaust port comprises a fixed aperture larger than an inlet aperture and larger than a channel for the nare of the patient, the fixed aperture disposed overlapping the flow splitter; and altering an exhaust role of the exhaust port to entrain an excess inhalation flow in response to a patient demand exceeding a flow rate of the single gas jet flow.

14. The method of claim 13, further comprising:

channeling the single gas jet flow after splitting to a device selected from a group consisting of: nasal prongs and a mask.

15. The method of claim 13, wherein diverting the single gas jet flow through an exhaust port comprises deflecting the single gas jet flow with an exhalation flow.

16. The method of claim 13, further comprising:

providing a patient exhalation flow and the single gas jet flow through the exhaust port during an exhalation phase.

17. The method of claim 13, wherein the single gas jet flow supplies gas for two nares of an infant.

18. The method of claim 13, further comprising:

measuring pressure via a pressure measurement port in each of two channels associated with each of the nares of the patient.

19. The method of claim 18, further comprising:

monitoring the pressure of each of the two channels via a pressure monitoring port.

* * * * *